United States Patent [19]

Maerkl et al.

[11] Patent Number: 4,755,625

[45] Date of Patent: Jul. 5, 1988

[54] PREPARATION OF 1,1,2-TRIALKOXYETHANES

[75] Inventors: Robert Maerkl, Fussgoenheim; Werner Bertleff, Viernheim; Rudolf Kummer, Frankenthal, all of Fed. Rep. of Germany

[73] Assignee: BASF Aktiengesellschaft, Ludwigshafen, Fed. Rep. of Germany

[21] Appl. No.: 73,999

[22] Filed: Jul. 16, 1987

[30] Foreign Application Priority Data

Aug. 16, 1986 [DE] Fed. Rep. of Germany ....... 3627776

[51] Int. Cl.$^4$ .............................................. C07C 43/315
[52] U.S. Cl. ..................................... 568/600; 549/347; 549/374; 549/453
[58] Field of Search ................. 568/600; 549/347, 374, 549/453

[56] References Cited

U.S. PATENT DOCUMENTS 2,449,470 9/1948 Gresham et al. .
4,071,568 1/1978 Onoda et al. .

FOREIGN PATENT DOCUMENTS 1359372 7/1974 United Kingdom .

Primary Examiner—Howard T. Mars
Attorney, Agent, or Firm—John H. Shurtleff

[57] ABSTRACT

1,1,2-trialkoxyethanes I

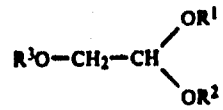

where $R^1$, $R^2$ and $R^3$ are each $C_1$–$C_8$-alkyl and $R^1$ and $R^2$ may furthermore be bonded to one another to form a 5-membered to 7-membered ring, are prepared by reacting a formaldehyde dialkyl acetal II with carbon monoxide and hydrogen, from 0.5 to 1.5 moles of hydrogen being used per mole of carbon monoxide, and with not less than 1 mole of alcohol $R^3OH$ per mole of formaldehyde dialkyl acetal under superatmospheric pressure and at elevated temperatures in the presence of a catalyst which is formed from a cobalt carbonyl compound and a trivalent organic compound of the formula III

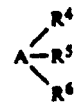

where A is phosphorus, arsenic, antimony or bismuth and $R^4$, $R^5$ and $R^6$ are each an organic radical.

10 Claims, No Drawings

PREPARATION OF 1,1,2-TRIALKOXYETHANES

The present invention relates to a process for the preparation of 1,1,2-trialkoxyethanes.

1,1,2-trialkoxyethanes are versatile intermediates for organic syntheses. For example, they can be subjected to acetal cleavage to give alkoxyacetaldehydes, which can be converted to polyols by condensation with formaldehyde. Furthermore, by eliminating alcohol, it is possible to prepare dialkoxyethenes, eg. dimethoxyethene, which are used as starting materials for polymers.

German Laid-Open Application DOS No. 2,048,272 discloses that 1,1,2-trimethoxyethanes can be obtained by reacting 1-chloro-2,2-dimethoxyethane or 1,1-dichloro-2-methoxyethane with an alkali metal methylate. However, 20% of methyl orthoacetate is formed as a byproduct. Another disadvantage of this process is that the production of an alkali metal chloride cannot be avoided.

It is an object of the present invention to provide a process for the preparation of 1,1,2-trialkoxyethanes which gives the products in good yields without producing salts.

We have found that this object is achieved by a process for the preparation of 1,1,2-trialkoxyethanes of the formula I

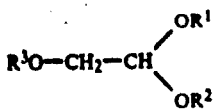
(I)

where $R^1$, $R^2$ and $R^3$ are each $C_1$–$C_8$-alkyl and $R^1$ and $R^2$ may furthermore be bonded to one another to form a 5-membered to 7-membered ring, wherein a formaldehyde dialkyl acetal II is reacted with carbon monoxide and hydrogen, from 0.5 to 1.5 moles of hydrogen being used per mole of carbon monoxide, and with not less than 1 mole of alcohol $R^3OH$ per mole of formaldehyde dialkyl acetal under superatmospheric pressure and at elevated temperatures in the presence of a catalyst which is formed from a cobalt carbonyl compound and a trivalent organic compound of the formula III

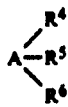
III where A is phosphorus, arsenic, antimony or bismuth and $R^4$, $R^5$ and $R^6$ are each an organic radical.

The fact that the process is successful is surprising since German Laid-Open Application DOS No. 2,655,406 discloses that hydroformylation of a formaldehyde dialkyl acetal in the presence of a catalyst formed, for example, from dicobalt octacarbonyl and a trialkylphosphine and in the presence of an inert solvent, eg. toluene, gives ethylene glycol in a yield of about 67%. The formation of a trialkoxyethane is not described. In addition to ethers and aliphatic or aromatic hydrocarbons, other inert solvents mentioned are alcohols. The $CO/H_2$ ratio is said not to be critical for the reaction and can be from 0.1 to 10 moles of $H_2$ per mole of CO. In all of the Examples, a large excess of hydrogen is used.

Starting compounds used for the novel process are formaldehyde dialkyl acetals II

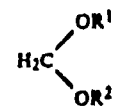
II where $R^1$ and $R^2$ are identical or different $C_1$–$C_8$-alkyl radicals or are bonded to one another to form a 5-membered to 7-membered ring. $R^1$ and $R^2$ are each preferably a primary or secondary $C_1$–$C_4$-alkyl radical, in particular methyl. Examples are methyl, ethyl, propyl, isopropyl, butyl and isobutyl. Examples of cyclic acetals are 1,3-dioxolane and 1,3-dioxane. Instead of the acetals II, it is also possible to use their precursors, ie. formaldehyde or compounds which liberate formaldehyde under the reaction conditions, eg. paraformaldehyde or trioxane, and the corresponding alcohols, the ratio of aldehyde to alcohol not being particularly critical. Advantageously, from 1 to 5 moles of alcohol are used per mole of aldehyde. Acetals whose alcohol components correspond to the alcohol $R^3OH$ used for the reaction are particularly preferably reacted.

$C_1$–$C_8$-alcohols, preferably $C_1$–$C_4$-alcohols, in particular methanol, are used as alcohols $R^3OH$. The following alcohols may be listed as examples: methanol, ethanol, propanol, isopropanol, n-butanol, isobutanol, tert-butanol, n-pentanol, isoamyl alcohol, neopentyl alcohol, n-hexanol, hexan-2-ol, n-heptanol and n-octanol.

The formaldehyde dialkyl acetal II is reacted with not less than an equimolar amount of alcohol $R^3OH$. The alcohol can advantageously be used in excess, for example from 1 to 5, preferably from 1.1 to 4, in particular from 1.5 to 2.5, moles of alcohol $R^3OH$ per mole of acetal. Larger excesses are possible but are of no further advantage.

The hydroformylation of the acetals II is carried out using a carbon monoxide/hydrogen mixture which contains from 0.5 to 1.5 moles, in particular from 0.5 to 1 mole, of hydrogen per mole of carbon monoxide. The molar ratio of CO to $H_2$ is preferably 1:1.

The process according to the invention is carried out in the presence of a complex catalyst which is formed from a cobalt carbonyl compound and a trivalent organic compound III

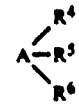
III where A is phosphorus, arsenic, antimony or bismuth and $R^4$, $R^5$ and $R^6$ are each an organic radical, eg. alkyl, cycloalkyl, alkoxy, aryl or aryloxy.

The cobalt carbonyl compound used can be, for example, dicobalt octacarbonyl or $HCo(CO)_4$. The cobalt carbonyl compounds can also be prepared in situ from cobalt compounds which, under the reaction conditions, are capable of forming cobalt carbonyl complexes, such as cobalt salts of organic or inorganic acids, eg. cobalt acetate, cobalt laurate, cobalt nitrate, cobalt sulfate or cobalt halides, or from cobalt oxide.

Preferably used compounds III are sparingly volatile triorganophosphorus compounds, trialkyl- and triarylphosphines and trialkyl and triaryl phosphites being particularly interesting from an economic point of view.

Triarylphosphines, such as triphenylphosphine or tritolylphosphine, and in particular trialkylphosphines in which $R^4$, $R^5$ and $R^6$ are each $C_1$–$C_8$-alkyl, eg. tributyl-, triisopropyl- or trioctylphosphine, are preferred. $R^4$, $R^5$ and $R^6$ may furthermore be $C_5$–$C_7$-cycloalkyl, eg. cyclohexyl. Instead of the stated phosphines, it is also possible to use the corresponding tertiary phosphites, such as triphenyl or tributyl phosphite.

Economical alkylarylphosphines, such as diphenyl-$C_1$–$C_8$-alkylphosphines or $C_1$–$C_8$-dialkylphenylphosphines, are also noteworthy.

The catalyst is advantageously prepared in situ from the cobalt carbonyl compound or its precursors and compound III. However, it is also possible for the complexes, such as $HCo(CO)_3(PR^4, R^5, R^6)$ or $Co_2(CO)_6$—$(PR^4, R^5, R^6)$, etc., to be prepared separately in a conventional manner and then added to the reaction mixture.

The atomic ratio of phosphorus to cobalt is in general from 0.1 to 1.2, preferably from 0.3 to 0.9.

Advantageously, cobalt concentrations and phosphine concentrations of from 1 to 5 mol %, based on the formaldehyde dialkyl acetal II, can be chosen. Higher concentrations are possible but are of little interest from an economic point of view.

The novel process can be carried out in the presence or absence of a solvent. Examples of suitable solvents are ethers, such as diethyl or diphenyl ether, aromatic or aliphatic hydrocarbons, such as benzene, toluene or hexane, and alcohols. The alcohols $R^3OH$ required for the reaction are advantageously also used as solvents.

The reaction can be carried out batchwise or, preferably, continuously under from 100 to 700, in particular from 200 to 400, bar and at from 50° to 300° C., preferably from 100° to 250° C., by a conventional method.

After the reaction, the trialkoxyethane I can be isolated from the mixture in a conventional manner, for example by distillation. The catalyst remains in the distillation residue and can be reused for the process according to the invention.

EXAMPLE 1

645 g (8.50 moles) of formaldehyde dimethyl acetal and 272 g (18.5 moles) of methanol were hydroformylated in an autoclave in the presence of 24.2 g (0.07 mole) of dicobalt octacarbonyl and 25.1 g (0.09 mole) of tributylphosphine at 150° C. and under 280 bar in the course of 2 hours, the ratio of CO to $H_2$ being 1:1. The mixture discharged contained 252 g (3.35 moles) of formaldehyde dimethyl acetal and 372 g (3.1 moles) of trimethoxyethane, corresponding to a yield of 60%, based on converted formaldehyde dimethyl acetal.

EXAMPLE 2

645 g (8.50 moles) of formaldehyde dimethyl acetal, 272 g of methanol, 24.2 g (0.07 mole) of dicobalt octacarbonyl and 25.5 g (0.09 millimole) of hexyldiphenylphosphine were reacted at 150° C. and under 280 bar by a method similar to that described in Example 1. The conversion of formaldehyde dimethyl acetal was 47% (4.0 moles), and the selectivity with respect to trimethoxyethane was 70%.

We claim:

1. A process for the preparation of a 1,1,2-trialkoxyethane of the formula I

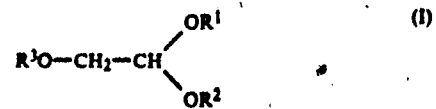

where $R^1$, $R^2$ and $R^3$ are each $C_1$–$C_8$-alkyl and $R^1$ and $R^2$ may furthermore be bonded to one another to form a 5-membered to 7-membered ring, wherein a formaldehyde dialkyl acetal II is reacted with carbon monoxide and hydrogen, from 0.5 to 1.5 moles of hydrogen being used per mole of carbon monoxide, and with not less than 1 mole of alcohol $R^3OH$ per mole of formaldehyde dialkyl acetal under superatmospheric pressure and at elevated temperatures in the presence of a catalyst which is formed from a cobalt carbonyl compound and a trivalent organic compound of the formula III

where A is phosphorus, arsenic, antimony or bismuth and $R^4$, $R^5$ and $R^6$ are each an organic radical.

2. A process as claimed in claim 1, wherein $R^1$, $R^2$ and $R^3$ are identical.

3. A process as claimed in claim 1, wherein from 1 to 5 moles of alcohol $R^3OH$ are used per mole of formaldehyde dialkyl acetal.

4. A process as claimed in claim 1, wherein from 1.5 to 2.5 moles of alcohol $R^3OH$ are used per mole of formaldehyde dialkyl acetal.

5. A process as claimed in claim 1, wherein from 0.5 to 1 mole of hydrogen is used per mole of carbon monoxide.

6. A process as claimed in claim 1, wherein equimolar amounts of carbon monoxide and hydrogen are used.

7. A process as claimed in claim 1, wherein the catalyst is formed from a cobalt carbonyl compound and a tertiary phosphine.

8. A process as claimed in claim 1, wherein the tertiary phosphine used is trialkylphosphine.

9. A process as claimed in claim 1, wherein the reaction is carried out at from 50° to 300° C.

10. A process as claimed in claim 1, wherein the reaction is carried out under from 100 to 700 bar.

* * * * *